| United States Patent [19] | [11] 3,968,242 |
|---|---|
| Gallo et al. | [45] July 6, 1976 |

[54] SULFONAMIDOAMINOPROPIOPHENONE INTERCEPTIVE PROCESS

[75] Inventors: Duane G. Gallo; William T. Comer, both of Evansville, Ind.

[73] Assignee: Mead Johnson & Company, Evansville, Ind.

[22] Filed: Aug. 26, 1974

[21] Appl. No.: 500,808

[52] U.S. Cl.............................. 424/321; 424/244; 424/274
[51] Int. Cl.² ....................................... A61K 31/18
[58] Field of Search ..................................... 424/321

[56] References Cited
UNITED STATES PATENTS 3,341,584  9/1967  Larsen et al.................... 424/246 X Primary Examiner—Norman A. Drezin
Assistant Examiner—Allen J. Robinson
Attorney, Agent, or Firm—Robert H. Uloth; Robert E. Carnahan

[57] ABSTRACT

A process for interrupting pregnancy is disclosed which comprises administration to a mammal an interceptive agent selected from a group of sulfonamidoaminopropiophenones. Illustrative of sulfonamidoaminopropiophenone interceptive agents useful in the process of the present invention for interrupting pregnancy are 4'-[3-(benzylmethylamino)propionyl]methanesulfonanilide and 4'-(3-hexamethyleniminopropionyl)methanesulfonanilide.

6 Claims, No Drawings

SULFONAMIDOAMINOPROPIOPHENONE INTERCEPTIVE PROCESS

BACKGROUND OF THE INVENTION

This invention relates to drug and body treating compositions and is particularly concerned with a process for interrupting pregnancy by administration of a p-sulfonamidoaminopropiophenone interceptive agent after implanation of the fertilized ovum.

At the present time, there are a number of available oral contraceptives containing estrogenic and progestational steroids that inhibit pregnancy by preventing ovulation if administered on an almost daily regimen. But, after fertilization and implantation of the ovum, there is presently little, short of mechanical (vacuum aspiration) or surgical abortion, that can be done to prevent delivery of viable offspring. Thus, there remains a large unmet need for a safe medication which requires infrequent or at the most only short periods of treatment to induce elimination of unwanted embryos. For the purpose of this disclosure, agents that interrupt pregnancy after implanation of the fertilized ovum are called "interceptives", as opposed to the term "contraceptives" which applies to agents that prevent pregnancy by inhibiting conception; refer to R. H. Naqvi, et al., Steroids, 18:731, 1971.

The p-sulfonamidoaminopropiophenones useful in the present invention are generically disclosed by A. A. Larsen, et al., U. S. Pat. No. 3,341,584. It was not recognized, however, until the present discovery that some of the p-sulfonamidoaminopropiophenones of the class disclosed by Larsen, et al. are effective interceptive agents.

SUMMARY OF THE INVENTION

The invention is concerned with a process for interrupting pregnancy in a mammal. In particular, the invention relates to the use of p-sulfonamidoaminopropiophenones of Formula I below to interrupt pregnancy after implantation has taken place. Non-toxic pharmaceutically acceptable acid addition salts of the compounds of Formula I are also effective in the process of the invention.

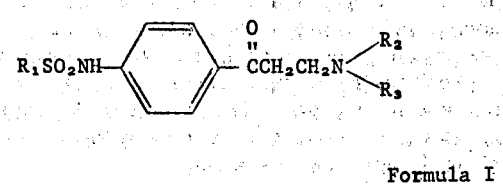

Formula I

In Formula I, $R_1$ represents methyl or ethyl and $R_2$ is methyl. The substituent $R_3$ can be straight or branched chain lower alkyl of 1 to 5 carbon atoms inclusive, and in addition, represents aralkyl groups of up to 10 carbon atoms inclusive. The $R_2$ and $R_3$ substituents taken together with the nitrogen atom to which they are attached represent a heteromonocycle having from 4 to 8 carbon atoms inclusive.

Compounds characterized by Formula I which are useful in the process of the present invention are obtained by reaction of a sulfonamidophenone of Formula II

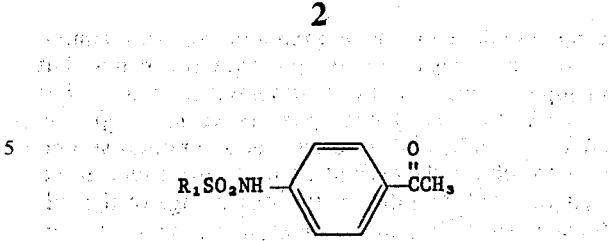

Formula II with formaldehyde and an amine of Formula III

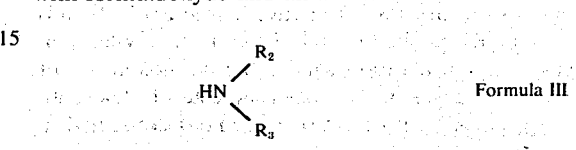

Formula III wherein $R_1$, $R_2$ and $R_3$ have the meanings hereinabove given for Formula I. This reaction is an application of the well known Mannich reaction involving aminomethylation of ketones and can be carried out in accordance with procedures and experimental procedures described in Organic Reactions, Vol. 1, Chapter 10, (Wiley, New York, 1942), Organic Syntheses, Coll. Vol. III, p. 305 (Wiley, New York).

The term "non-toxic pharmaceutically acceptable acid addition salts" as used herein refers to salts of the sulfonamidoaminoketones of Formula I with relatively non-toxic inorganic or organic acids. Illustrative of non-toxic pharmaceutically acceptable acid addition salts of compounds characterized by Formula I are the salts of inorganic or organic acids such as sulfuric, phosphoric, hydrochloric, hydrobromic, hydroiodic, sulfamic, acetic, lactic, malic, succinic, maleic, fumaric, tartaric, citric, gluconic, glutaric, ascorbic, benzoic, cinnamic, methanesulfonic, ethanesulfonic, p-toluenesulfonic, isethionic, and other related acids.

Preparation of pharmaceutically acceptable acid addition salts of the compounds of Formula I is accomplished by admixture of the sulfonamidoketone bases with at least one chemical equivalent of any of the various acids hereinabove listed. Generally, the salts are prepared in a reaction inert solvent such as ether, benzene, ethanol, methanol, ethyl acetate, acetone, acetonitrile, chloroform, water and the like.

According to the process of the present invention for interrupting pregnancy, the compounds of Formula I and pharmaceutically acceptable acid addition salts thereof are administered in effective doses orally or parenterally, e.g., by intramuscular, intravenous, intraperitoneal, or subcutaneous injection, to a pregnant mammal during a critical stage of embryonic development wherein the embryo is subject to interception in an effective dose to interrupt pregnancy. For the purpose of this disclosure, the "critical stage of embroynic development wherein the embryo is subject to interception" referred to herein is also designated the "interceptive stage".

The term "effective dose" used herein refers to the amount of an interceptive agent of Formula I which is required to interrupt pregnancy when administered during the interceptive stage which occurs at a specific time for each species after implantation of the fertilized ovum. The amount of an "effective dose" ranges from 20 to 500 mg./kg. body weight. Preferably an effective amount of an interceptive agent of Formula I is administered in a single dose to interrupt pregnancy, but multiple dosing can also be employed if desired. For instance, doses which by themselves are not completely effective can be administered over a period of several days to achieve the desired effect It will be recognized by those skilled in the art that the dosage of the sulfonamidoaminopropiophenones of Formula I employed in carrying out the process of the present invention for interrupting pregnancy in mammals will vary with the form and mode of administration, with the species of mammal, and to some degree with the particular interceptive agent chosen. Dosage figures given herein refer to the dose of "active ingredient" which is a term applied to the Formula I free bases. When employing an acid addition salt of the aminoketones of Formula I, the size of the dose is adjusted to take into account the percent of active ingredient contained in the salt.

Compounds particularly preferred for practicing the process of the present invention are:

4'-(3-hexamethyleniminopropionyl)methanesulfonanilide,

4'-[3-(benzylmethylamino)propionyl]methanesulfonanilide,

4'-[3-(1-pyrrolidinyl)propionyl]methanesulfonanilide,

4'-(3-dimethylaminopropionyl)methanesulfonanilide.

The interceptive agents of Formula I and their pharmacologically acceptable acid addition salts are relatively non-toxic and substantially free from other pharmacological effects upon oral or parenteral administration to a mammal at doses which produce the interceptive effect. For instance, the approximate oral $LD_{50}$ value in mice for 4'-[(3-benzylmethylamino)propionyl]methanesulfonanilide hydrochloride is greater than 2000 mg./kg. while the oral dose which produced a 100% interceptive effect in the rat was 383 mg./kg. body weight.

To determine the critical embryonic stage in a mammal following fertilization wherein embryonic development may be intercepted, i.e., the interceptive stage, an interceptive agent of Formula I is administered to different groups of animals at various times after implantation of the fertilized ovum in accord with accepted pharmacological procedures. For example, a maximally tolerated dose of the interceptive agent is administered to a pregnant mammal at intervals related to the duration of gestation of the species being investigated beginning after implantation in accordance with the schedule suggested in Table I with a subsequent determination of whether pregnancy has been interrupted.

TABLE I

SUGGESTED FREQUENCY OF DOSING TO DETERMINE INTERCEPTIVE STAGE

| Gestation Length | Initial Dose After Implantation | Interval |
|---|---|---|
| 30 days | 3 days | 2 days |
| 31–60 days | 5 days | 3 days |
| 61–160 days | 8 days | 4 days |
| greater than 160 days | 12 days | weekly |

In lower mammals such as the mouse, rat, hamster, rabbit, guinea pig, interruption of pregnancy is established by autopsy. In more valuable mammals such as the pig, cow dog, and higher primates including the human, interruption of pregnancy can be readily determined by such means as transcervical examination of the uterine wall, laproscopic examination, rectal palpation of the uterus, and in higher primates onset of menses, all of which can be, if desired, supplemented with determination of urinary and/or blood pregnancy associated hormone levels. After the "interceptive stage" is established, the minimally effective dose can be determined, if desired, by administering various doses of the interceptive agent in accord with standard pharmacological procedures.

The interceptive stage of embryonic development for representative mammalian species determined by oral administration of the interceptive agents of Formula I as described hereinabove is given in Table II.

TABLE II

APPROXIMATE INTERCEPTIVE STAGE OF EMBRYONIC DEVELOPMENT

| Mammalian Species | Days Following Fertilization |
|---|---|
| Rat | 10–12 |
| Mouse | 10–12 |
| Hamster | 9–15 |
| Rabbit | 11–18 |
| Guinea Pig | 14–34 |

In higher primates, the process of the invention may also be considered a process for inducing menses. In this instance, absence of a menstrual flow is considered indicative of pregnancy and menses is induced by administering an effective dose of compounds of Formula I commencing 1 to 2 weeks after the expected onset of menstrual flow.

Interceptive agents characterized by Formula I can be employed in admixture with the usual pharmaceutical carriers in carrying out the process of the present invention for interrupting pregnancy. Those organic and inorganic pharmaceutical carrier substances suitable for oral and parenteral application such as water, vegetable oils, polyethylene glycol, gelatin, lactose, starch, magnesium stearate, talc, and the like are operable. For oral administration, tablets, capsules, powders, granules, syrups, elixirs, liquid suspensions, or solutions are preferred. The interceptive agents of Formula I can be incorporated with a pharmaceutical carrier in unit dosages providing from 250 to 2000 mg. of active ingredient and effective amounts thereof are administered to mammals in practicing the process of the present invention for interrupting pregnancy.

The following examples are given to further illustrate the present invention. They are merely illustrative and are not to be construed as limiting the scope of the claims in any manner whatsoever.

DESCRIPTION OF SPECIFIC EMBODIMENTS

EXAMPLE 1

EFFECT OF A SINGLE ORAL DOSE OF 4'-[3-(BENZYLMETHYLAMINO)PROPIONYL]-METHANESULFONANILIDE HYDROCHLORIDE ON PREGNANCY RATE IN THE RAT AND RABBIT

Mature female rats of the Harlan-Wistar strain weighing between 200 and 300 g. were mated to males of the same strain and divided into groups of 10. For the purpose of this experiment, day 1 of pregnancy was designated as that day on which sperm were first observed in a vaginal smear after caging the animals together. Animals of one group served as a control while varying doses of 4'-[3-(benzylmethylamino)propionyl]methanesulfonanilide hydrochloride in an appropriate pharmaceutical vehicle such as water were administered orally to other groups on day 11 (the day of pregnancy midway in the interceptive stage of embryonic development). The animals were sacrificed a suitable period after dosing such as 5–10 days and the uteri were examined for the number and condition of implantation sites. Animals exhibiting at least one normal implantation site were considered to be pregnant while those showing no evidence of an implantation site were excluded from the experiment. The foregoing procedure was repeated with rabbits except that ovulation was artificially induced by injected human chorionic gonadotropin and pregnancy induced by artificial insemination. Results obtained are listed below:

| Mammal | Day of Pregnancy Administered | Oral Dose (mg./kg.) | Percent Pregnant |
| --- | --- | --- | --- |
| Rat | 11 | 0 | 88 |
| | | 96 | 100 |
| | | 192 | 86 |
| | | 288 | 11 |
| | | 383 | 0 |
| Rabbit | 15 | 0 | 100 |
| | | 31 | 25 |
| | | 58 | 0 |

EXAMPLES 2–4

Results are given below for other representative sulfonamidoaminopropiophenone hydrochloride salts of Formula I administered orally as a single dose to rats on day 11 of pregnancy and rabbits on day 15 of pregnancy in accordance with the procedure of Example 1.

EXAMPLE 2

4'-(3-Hexamethyleniminopropionyl)methanesulfonanilide

| | Dose Millimole/kg. | Percent Pregnant |
| --- | --- | --- |
| Rat | 0 | 88 |
| | 0.25 | 100 |
| | 0.5 | 67 |
| | 0.75 | 50 |
| | 1.0 | 0 |
| Rabbit | 0 | 100 |
| | 0.15 | 100 |
| | 0.22 | 60 |
| | 0.3 | 25 |

EXAMPLE 3

4'-[3-(1-Pyrrolidinyl)propionyl]methanesulfonanilide

| | Dose Millimole/kg. | Percent Pregnant |
| --- | --- | --- |
| Rat | 0 | 100 |
| | 1 | 100 |
| | 2 | 50 |
| | 2.25 | 10 |
| | 4.5 | 0 |
| Rabbit | 0 | 100 |
| | 1.5 | 33 |

EXAMPLE 4

4'-(3-Dimethylaminopropionyl)methanesulfonanilide

| | Dose Millimole/kg. | Percent Pregnant |
| --- | --- | --- |
| Rat | 0 | 100 |
| | 2 | 43 |
| | 3 | 38 |
| | 4.5 | 0 |

Preparation of Formula I
Sulfonamidoaminopropiophenones

In order to assure that the interceptive agents employed in the process of the present invention are readily available, descriptions of preparations of representative Formula I compounds are given below.

Compound 1

Substitution of an equimolar amount of N-methylbenzylamine hydrochloride for pyrrolidine hydrochloride in the procedure of Compound 3 provides analytically pure 4'-[3-(benzylmethylamino)propionyl]METHANESULFONANILIDE HYDROCHLORIDE, m.p. 176°–178°C. (corr). by crystallization from methanol-isopropyl alcohol.

Analysis. Calcd. for $C_{18}H_{22}N_2O_3S \cdot HCl$: C, 56.46; H, 6.05; N, 7.32. Found: C, 56.45; H, 6.32; N, 7.18.

Compound 2

Substitution of an equimolar amount of hexamethylenimine hydrochloride for pyrrolidine hydrochloride in the procedure of Compound 3 provides analytically pure 4'-(3-HEXAMETHYLENIMINOPROPIONYL)METHANESULFONANILIDE HYDROCHLORIDE, m.p. 171°–173.5°C. (corr.) by crystallization from methanol.

Analysis. Calcd. for $C_6H_{24}N_2O_3S \cdot HCl$: C, 53.24; H, 6.98; Cl, 9.83. Found: C, 53.20; H, 6.95; Cl, 9.75.

Compound 3

A mixture of 4'-acetylmethanesulfonanilide (21.5 g., 0.1 mole), 95% paraformaldehyde (10 g., 0.3 mole), pyrrolidine hydrochloride (10.8 g., 0.1 mole) in 150 ml. of ethanol containing 1 drop of concentrated hydrochloric acid is refluxed for a period of 4 hr. at steam bath temperature and then for an additional period of 8 hr. permitting the ethanol to evaporate. The resulting glassy residue is stirred with 300 ml. of hot acetone providing a crystalline material which is collected and crystallized from methanol-isopropyl alcohol to afford analytically pure 4'-[3-(1-PYRROLIDINYL)PROPIONYL]-METHANESULFONANILIDE HYDROCHLORIDE, m.p. 182.0°–183.0°C.

Analysis. Calcd. for $C_{14}H_{20}N_2O_3S \cdot HCl$: C, 50.52; H, 6.36; N, 8.42. Found: C, 50.65; H, 6.48; N, 8.32.

Compound 4

Substitution of an equimolar amount of dimethylamine hydrochloride for pyrrolidine hydrochloride in the procedure of Compound 3 affords analytically pure 4'-(3-DIMETHYLAMINOPROPIONYL)METHANESULFONANILIDE HYDROCHLORIDE, m.p. 195°–197°C. (corr.), by crystallization from methanol-isopropyl alcohol.

Analysis. Calcd. for $C_{12}H_{18}N_2O_3S \cdot HCl$: C, 46.97; H, 6.24; N, 9.13. Found: C, 47.04; H, 6.28; N, 8.88.

Compound 5

Substitution of an equimolar amount of 4'-acetylethanesulfonanilide for 4'-acetylmethanesulfonanilide in the procedure of Compound 3 affords 4'-[3-(1-PYRROLIDINYL)PROPIONYL]-ETHANESULFONANILIDE.

Compound 6

Reaction of 4'-acetylethanesulfonanilide, formaldehyde and N-methylbenzylamine hydrochloride according to the procedure of Compound 3 affords 4'-[3-(BENZYLMETHYLAMINO)PROPIONYL]-ETHANESULFONANILIDE.

What is claimed is:

1. A process for interrupting pregnancy in a pregnant female mammal capable of resorbing an implanted fertilized ovum comprising orally or parenterally administering to said mammal an interceptive agent during the interceptive stage in an effective dose to cause resorption of said implanted fertilized ovum and said interceptive agent is a p-sulfonamidoaminopropiophenone of the formula

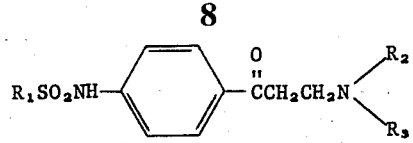

or a pharmaceutically acceptable acid addition salt thereof wherein
   $R_1$ is methyl or ethyl;
   $R_2$ is methyl; and
   $R_3$ is lower alkyl of 1 to 5 carbon atoms inclusive or aralkyl up to 10 carbon atoms inclusive.

2. The process of claim 1 wherein said effective dose is 20 to 500 mg./kg. body weight.

3. The process of claim 1 wherein said interceptive agent is 4'-[3-(benzylmethylamino)propionyl]methanesulfonanilide.

4. The process of claim 1 wherein said interceptive agent is 4'-[3-(benzylmethylamino)propionyl]methanesulfonanilide hydrochloride.

5. The process of claim 1 wherein said interceptive agent is 4'-(3-dimethylaminopropionyl)methanesulfonanilide.

6. The process of claim 1 wherein said interceptive agent is 4'-(3-dimethylaminopropionyl)methanesulfonanilide hydrochloride.

* * * * *